United States Patent [19]

Franolic et al.

[11] Patent Number: 5,717,121

[45] Date of Patent: Feb. 10, 1998

[54] PREPARATION AND USE OF CONTRAST AGENTS

[75] Inventors: John D. Franolic; Jeffrey R. Long; Richard H. Holm, all of Cambridge, Mass.; Michael Droege, Livermore; Shannan Downey, Sunnyvale, both of Calif.

[73] Assignee: Nycomed Salutar, Inc., Wayne, Pa.

[21] Appl. No.: 481,152

[22] Filed: Jun. 7, 1995

[51] Int. Cl.$^6$ .............................. C07F 11/00; C07F 9/00; C07F 7/00

[52] U.S. Cl. .............................. 556/57; 556/43; 556/52; 556/56

[58] Field of Search .................. 556/57, 43, 52, 556/56

[56] References Cited

FOREIGN PATENT DOCUMENTS

93/02713  2/1993  WIPO .

OTHER PUBLICATIONS

Inorganic Chemistry, vol. 12, No. 10, Easton US, pp. 2356–2361, XP002021635, A.D. Westland et al. "Reactions of Halocarbonyls of Group VIB Elements.II Complexes of Molybdenum and Tungsten Containing Group VA Donors or Phenyl Isocynaide." (1973).

Chemical Abstracts, vol. 102, No. 24, Jun. 17, 1985, Columbus, Ohio, US; abstract No. 214063, Schaefer, Harald et al.: "Tungsten/iodine system", XP002021934, see abstract & Z. Anorg. Allg. Chem. (1984), 516, 196–200 CODEN: ZAACAB; ISSN: 0044–2313, 1984.

Schulz et al., Chemical Abstracts, vol. 73, No. 22, Chemical Abstract No. 115864j, p. 460 (1970).

Franolic et al., Journal of American Chemical Society, vol. 117, No. 31, pp. 8139–8153 (1995).

*Primary Examiner*—Porfirio Nazario-Gonzalez
*Attorney, Agent, or Firm*—Fish & Richardson P.C.

[57] ABSTRACT

A process for the preparation of multinuclear cluster compounds by reacting a metal carbonyl with iodine, and use of these clusters and clusters derived from them, in diagnostic imaging. Novel multinuclear cluster compounds are also disclosed.

6 Claims, No Drawings

PREPARATION AND USE OF CONTRAST AGENTS

The present invention relates to the preparation and use in diagnostic imaging, in particular X-ray imaging, of contrast agents comprising multinuclear moieties, and to contrast media containing such moieties.

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedure, i.e. increased contrast can lead to increased spatial resolution.

The diagnostic quality of images is strongly dependent on the inherent noise level in the imaging procedure—and the ratio of the contrast level to the noise level can thus be seen to represent an effective diagnostic quality factor for diagnostic images.

Achieving improvement in such a diagnostic quality factor has long been and still remains an important goal. In techniques such as X-ray and ultrasound, one approach to improving the diagnostic quality factor has been to introduce contrast enhancing materials, contrast agents, into the body region being imaged.

Thus in X-ray for example early examples of contrast agents were insoluble inorganic barium salts which enhanced X-ray attenuation in the body zones into which they distributed. More recently the field of X-ray contrast agents has been dominated by soluble iodine containing compounds such as those marketed by Nycomed AS under the trade names Omnipaque and Amipaque.

Much recent work on X-ray contrast agents has concentrated on aminopolycarboxylic acid (APCA) chelates of heavy metal ions and, recognising that effective imaging of many body sites requires localization at the body sites in question of relatively high concentrations of the metal ions, there have been suggestions that polychelants, that is substances possessing more than one separate chelant moiety, might be used to achieve this.

More recently it has been found that contrast enhancement may be achieved particularly effectively by the use of multinuclear complexes, that is complexes wherein the complexed moiety itself comprises two or more contrast enhancing atoms or for X-ray two or more heavy atoms. See WO91/14460 and WO92/17215.

For the sake of clarity, the word "atom" is used to refer to ionic and covalently bonded forms and not simply to isolated uncharged atoms. Moreover it will be understood that the complexed moiety, while it is polynuclear, is not so large as to be considered to be a particle itself. Thus it will generally have maximum dimensions of 80 Å or less, especially 40 Å or less.

The present invention relates to improvements in such multinuclear moieties and provides in a first aspect a process for the preparation of a compound of formula

 (I)

(where $M_n B_u A_v$ is a multinuclear entity; each M is a heavy metal atom selected from W, Mo, Ta, Nb and Hf; each metal atom M is covalently bonded to at least one, preferably 2–6, atoms; each B is a bridging atom covalently bonded to at least two, preferably 2 or 3, metal atoms M; each A which may the same or different is a non-bridging atom covalently bonded to a metal atom M; n and u are positive integers of value 2 or greater; and v is zero or a positive integer) or a salt, especially a physiologically tolerable salt, thereof, comprising reacting $M(CO)_6$ and $I_2$ for a time and at a temperature sufficient to form a metal/iodine cluster, and optionally displacing one or more non-bridging or bridging iodine atoms in said cluster with one or more further atoms or radicals to form a modified cluster and/or formation of a salt of said cluster or modified cluster.

In formula I above n, u and v are preferably 2 to 30, especially 2 to 10, particularly 2 to 8; n is even more preferably 2 to 6.

Certain of the clusters which can be formed by the above process are new and form an aspect of the present invention in their own right. Thus the invention provides compounds of formula

 (II)

in which n is 3, 4 or 5, preferably 4 or 5, and M, B, A, n, u and v are as defined above, and salts, especially physiologically tolerable salts thereof. Complexes in which n is 6 are known.

M in formulae (I) and (II) is preferably a molybdenum atom and especially preferably a tungsten atom. A and B are preferably iodine but may also be another halogen such as fluorine, chlorine or bromine; an oxygen atom, for example as part of a water molecule, an alcohol molecule (e.g. ethanol), a trifluoromethane-sulphonate or an acetate; a sulphur atom, for example as part of an isothiocyanate; a nitrogen atom, for example as part of an amine radical or an amino acid; or a phosphorus atom, for example as part of a phosphorus-containing radical. When A and B are oxygen, sulphur, nitrogen or phosphorus, they may from part of a larger ligand, for example a chelating ligand as discussed in more detail hereinafter. When B is carbon, oxygen, sulphur, nitrogen or phosphorus it need not form part of a larger ligand, in which case it will simply form a bridging structure.

A further aspect of the invention provides a diagnostic imaging contrast medium comprising a compound of formula (I) prepared according to the abovementioned process, or a compound of formula (II), complexed with one or more ligand molecules.

Viewed from a further aspect the invention provides compounds of formula (I) prepared according to the abovementioned process, and compounds of formula (II), for use as diagnostic imaging contrast agents.

Viewed from a still further aspect the invention provides a diagnostic imaging contrast medium comprising a compound of formula (I) prepared according to the abovementioned process, or a compound of formula (II), complexed with one or more ligand molecules, together with at least one sterile pharmaceutical carrier or excipient.

A yet further aspect of the invention provides a method of generating an image of a human or non-human animal, preferably mammalian, body which method comprises administering to said body a physiologically tolerable contrast enhancing amout of a compound of formula (I) prepared according to the abovementioned process, or a compound of formula (II), complexed with one or more ligand molecules, and generating an image, preferably an X-ray image, of at least said part of said body.

The metal/iodine compounds of formulae (I) and (II) are particularly advantageous in contrast media since they contain two excellent X-ray attenuators, a heavy metal and iodine. Thus contrast media based on these complexes are unique in providing the radiologist with a choice of the X-ray energies which may be used thus optimising the radiological procedure.

The solid state reaction between $M(CO_6)$ and $I_2$ for preparing compounds according to the present invention is effected by heating the reactants, for example at 140° C., to release CO gas, followed by further heating of the amorphous mixture to produce binary cluster phases. Lower temperatures (140°–220° C.) will tend to produce solid phases containing 3 to 4 metal atoms per cluster, increasing the temperature (250°–550° C.) produces pentanuclear and hexanuclear cluster phases. Discrete molecular clusters are obtained via dimensional reduction and/or direct solubilization of these cluster phases.

Substitution of non-bridging atoms by other atoms/groups to give a modified cluster can be effected by techniques known per se.

It has previously been proposed, for example, to react $W(CO)_6$ and $I_2$ to prepare mixed tungsten/iodine compounds. However, the resulting compounds have all been solid phases, not discrete clusters. See J. Less Common Metals 22, 136 (1970); Z. Anorg. Allg. Chem. 516, 196 (1984); Virmani et al. in J. Chem. Soc. Dalton Trans., 399 (1974); Djordjevic et al. in J. Chem. Soc. (A), 16 (1966); and Inorg. Chem. 12, 2356 (1973).

The compounds of formulae (I) and (II) may have the following preferred structures:

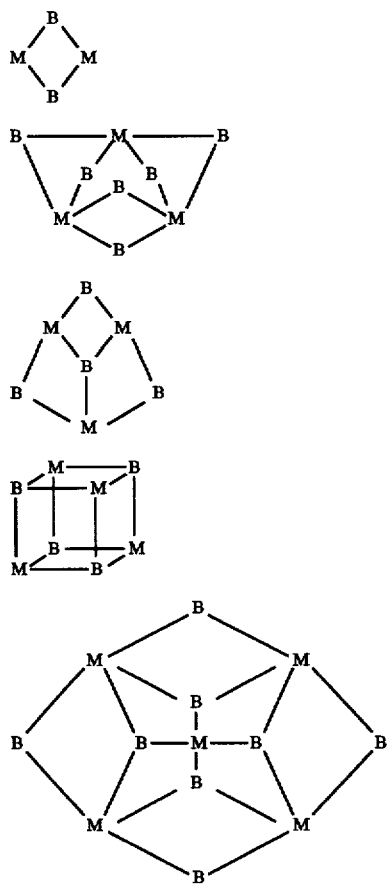

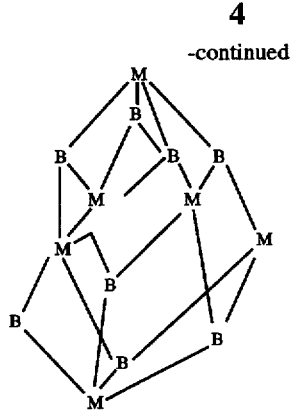

where each B which may be the same or different is a bridging iodine atom and each M is a metal atom, and where other non-bridging atoms covalently bonded to metal atoms M are omitted for the sake of clarity.

In the case of bridged structures of these formulae, the structural formulae can conveniently be written $M_2(\mu_2B)_2$, $M_3(\mu_2B)_6$, $M_4(\mu_3B)_4(\mu_2B)_4$, $M_4(\mu_3B)_4$ and $M_6(\mu_3B)_8$ respectively ($\mu_3B$ indicating for example that the B is a bridging atom bonded to 3 metals). As mentioned above, it is particularly preferred that the compounds form chelate complexes and it is especially preferred that a single multidentate chelant be used to coordinate at least two and preferably all of the liganded centres.

The process according to the invention can, when used with $W(CO)_6$, yield binary phases and/or molecular clusters with core units $[W_3I_6]^{2+}$, $[W_4I_7]^{3+}$, $[W_5I_8]^{3+,4+}$, $[W_5(C)I_8]^{4+}$, and $[W_6I_8]^{4+}$. A number of these compounds are obtained directly from reaction or solubilization of two phases, which we designate as Phase A and Phase B. These materials have not been previously examined, although as mentioned above reactions between their precursors, $W(CO)_6$ and iodine, have been explored under different conditions. Phase A can be formed when $W(CO)_6$ and 7 equivalents of iodine are heated at 140° C., liberating CO; washing this solid, for example with ether, removes unreacted iodine, producing washed Phase A. Any residual CO present is too dilute to detect by infrared spectroscopy. As probed by X-ray powder diffraction, washed Phase A typically contains a small amount of insoluble crystalline $W_4I_{13}$ while its major components are amorphous. Phase B is obtained directly from Phase A by heating it in a sealed tube, for example for 50 hours at 200° C. The black-gray product is washed (again ether is suitable) to remove unreacted iodine. Again, X-ray powder diffraction revealed the only crystalline component of Phase B to be occasional traces of $W_4I_{13}$; its primary constituent is amorphous.

Molecular $[W_3I_9]^{1-}$ can be obtained directly from washed Phase A by stirring it in THF for 24 hours and adding $(Bu_4N)I$ to the filtrate. The resulting solid may be washed with ethanol to remove triiodide salts, a procedure which is best carried out quickly, as the cluster itself is slightly soluble in ethanol. The final product may be recrystallized from dichloromethane. The FAB mass spectrum of washed Phase A in THF exhibits major peaks corresponding to $[W_6I_{18}]^{1-}$, $[W_6I_{17}]^{1-}$ and $[W_6I_{16}]^{1-}$, suggesting that the solid precursor of $[W_3I_9]^{1-}$ contains the cluster in dimeric form.

Varying amounts of $W_4I_{13}$ are observed in the reaction between $W(CO)_6$ and iodine at temperatures in the range 140°–200° C. The other products formed at this temperature are readily removed by repeated washing with ether and THF. The remaining black solid is crystalline $W_4I_{13}$ which proved insoluble in common solvents and acids. The compound forms molecular crystals in which two $[W_4I_7Ia_2]^{1+}$ units are linked by two triiodide ions. Two halves of such double clusters occur in the asymmetric unit; the halves of each double cluster are related by an inversion center.

When Phase B is completely dissolved in ethanol over the course of 18 hours, a new cluster, $[W_5I_{13}]^{1-}$, can be isolated in molecular form, for example as its $(Pr_4N)^+$ salt in 31% purified yield (based on $W(CO)_6$). A binary phase $W_5I_{16}$ has been observed when Phase A was heated at somewhat higher temperatures (250°–300° C.) than in the preparation of Phase B. The appearance of this phase at higher temperatures suggests its presence in amorphous form in the lower temperature preparations. We consider $W_5I_{16}$ (or possibly $W_5I_{14}xI_2$) as the logical precursor to $[W_5I_{13}]^{1-}$; both species contain tungsten in the mean 2.4+ oxidation state. Indeed, paralleling Phase B, the material containing $W_5I_{16}$ also yields $[W_5I_{13}]^{1-}$ when treated with ethanol and iodide.

The compound $(Pr_4N)[W_5I_{13}]$ is soluble in THF, dichloromethane, and acetone. When a deep-green solution in dichloromethane is treated with zinc metal over the course of 24 hours, the solution changes to brown-red. Upon the addition of excess cation, the compound $(Pr_4N)_2[W_5I_{13}]$ is isolated. The compound is air-stable in solid form; it is soluble in THF, dichloromethane, acetone, and acetonitrile, but its solutions slowly oxidize in air to $[W_5I_{13}]^{1-}$.

When Phase A is reacted with excess CsI at 300° C. for 50 hours, a brown-black solid mixture containing $[W_6I_{14}]^{2-}$, cesium iodides, and $CsW_5CI_{16}$ is formed. The crystal structure of this phase reveals it to be molecular in nature, containing individual $[W_5(C)I_{13}]^{1-}$ clusters; the asymmetric unit contains one cluster, one $Cs^+$, and one and one-half iodine molecules.

When the solid mixture is extracted with acetonitrile and the extract treated with $(Bu_4N)I$, the $(Bu_4N)^+$ salts of $[W_6I_{14}]^{2-}$ and $[W_5(C)I_{13}]^{1-}$ coprecipitate. Extraction of this material with THF followed by recrystallization of the residue from THF/hexane affords pure $(Bu_4N)[W_5(C)I_{13}]$. Evidently, some residual CO is reductively cleaved in the course of formation of $[W_5(C)I_{13}]^{1-}$. A possible intermediate is $[W_5(CO)I_{13}]^{2-}$, formed in the reaction tube when highly pressurized with CO. The compound is soluble in THF, dichloromethane, and acetone.

Maintenance of Phase B at 550° C. for 50 hours results in the deposition of $W_6I_{12}$ as an orange solid at one end of the reaction tube in 25% yield (based on $W(CO)_6$). The structure of $W_6I_{12}$ makes evident its two-dimensional nature and the connectivity $[W_6Ii_8]Ia_2Ia$-$a_{4/2}$. The $[W_6I_8]^{4+}$ core has the familiar face-capped octahedral structure found for $[M_6X_8]^{2+}$ units with M=Mo and W.

When unwashed Phase B is heated at 550° C. for 50 hours and the resultant solid washed with ether, red-brown $W_6I_{16}$ is obtained. The structure of this phase has the same two-dimensional connectivity as $W_6I_{12}$ but contains between the sheets two iodine molecules per cluster. The iodine-rich nature of this phase is attributed to free iodine present in unwashed Phase B.

When unwashed Phase B is heated in the range 400°–500° C., mixtures containing $W_6I_{12}$, $W_6I_{16}$ and a new phase, black $W_6I_{18}$ ($WI_3$), are produced at the hot end of the tube. Crystals of the latter phase are sometimes observed when tungsten metal and iodine are heated at 600°–800° C. Under both conditions, the yield of $W_6I_{18}$, identified by crystal habit (rods) after the initial structure determination, was so low as to be undetected by X-ray powder diffraction. A previous report (Z. Anorg. Allg. Chemie 516, 196 (1984)) describes the synthesis of "silver needles" which analyzed as $WI_{3.0}$ from two different sealed tube preparations: (1) reaction of tungsten metal and iodine in a 500°–350° C. temperature gradient; (2) chemical transport of "$WI_{3.3}$" in a 450°–350° C. temperature gradient. The latter is consistent with our observation that sealed tube reactions of Phase B conducted in a ca. 350°–400° C. range yield at the cooler end of the tube silver needles analyzing exactly as $WI_3$.

In past accounts, the preparation of soluble $[W_6I_8]^{4+}$ core containing species has generally proceeded via excision from $W_6I_{12}$ with ethanol/HI reaction mixtures, producing $[W_6I_{14}]^{2-}$ in solution. Although such methods readily excise the analogous phases $Mo_6X_{12}$ (X=Cl, Br, I) and $W_6X_{12}$ (X=Cl, Br), the technique has proven significantly less effective when applied to $W_6I_{12}$. In agreement with prior observations, we find $W_6I_{12}$ to be only sparingly soluble in ethanol/HI, leading to disappointingly low yields of $[W_6I_{14}]^{2-}$. Indeed, none of the previously reported syntheses of $[W_6I_{14}]^{2-}$ quantify a yield for this product. A much improved route to this cluster is attained by applying dimensional reduction to $W_6I_{12}$. In accordance with this formalism, incorporation of KI breaks up the two-dimensional framework of $W_6I_{12}$ producing a molecular solid of probable formula $K_2W_6I_{14}$ (analogous to $K_2Mo_6Cl_{14}$), which completely dissolves in ethanol to give the desired species $[W_6I_{14}]^{2-}$ in solution. In the present work, this was accomplished by heating Phase B and KI under conditions which in the absence of KI afford $W_6I_{12}$.

When an intimate mixture of Phase B and KI are heated at 550° C. for 65 hours, an orange-black solid is formed (presumably $K_2W_6I_{14}$) which contains the $[W_6I_{14}]^{2-}$ cluster anion. Dissolution of the solid in ethanol followed by addition of solid $(Bu_4N)I$ gave $(Bu_4N)_2[W_6I_{14}]$.

With regard to substitution of one ligand for another in the compounds of the invention, the clusters sustain core halide substitution reactions under forcing conditions, but exhibit relatively facile terminal ligand substitution reactions. We have chosen to replace iodide with triflate in order to obtain clusters of high substitutional lability for use in subsequent work. Following the procedure of Shriver and coworkers [Inorg. Chem. 31, 1869 (1992)] for $[Mo_6Cl_8(CF_3SO_3)_6]^{2-}$, $(Pr_4N)_2[W_5I_8(CF_3SO_3)_5]$ was obtained by the reaction of $(Pr_4N)_2[W_5I_{13}]$ and excess Ag $(CF_3SO_3)$ in dichloromethane. In an analogous reaction, $(Bu_4N)_2[W_6I_8(CF_3SO_3)_6]$ was isolated.

With regard to complexation of the compounds of the invention and their subsequent formulation as contrast media, it is particularly convenient for the compounds of formula (I) and (II) to be presented as their chelate complexes containing EDTA, DTPA or other APCA's. Such chelate complexes are remarkably stable with regard to release of the heavy metal ions or clusters.

It is particularly preferred that the electrical charge carried by the complexing moieties should substantially if not completely balance that carried by the complexed entity; for APCA chelants this may easily be achieved for example by omission, replacement or deactivation (e.g. by ester or amide formation) of one or more of the carboxyl moieties.

Many suitable chelants are widely known or have been described in the literature, especially literature relating to heavy metal detoxification agents bifunctional chelants and chelate-based contrast agents, e.g. those described in WO-A-89/00557 (Berg) and the documents mentioned therein and in the search report appended thereto, U.S. Pat. No. 4,647,447 (Gries), U.S. Pat. No. 4,826,673 (Dean), EP-A-230893 (Felder), EP-A-217577 (Frincke), U.S. Pat. No. 4,652,519 (Warshawsky), U.S. Pat. No. 4,687,659 (Quay), and numerous other recent patent publications of Nycomed AS, Salutar Inc, Schering AG, Squibb, Bracco, Mallinckrodt, Dow and Guerbet.

Thus polyamines, especially linear or cyclic polyamines, such as ethylenediamine, 1,4,7-triazacyclononane and cyclen, can be used as chelants, as can APCAs such as DTPA, EDTA and derivatives thereof and other cyclic and non-cyclic APCAs as defined in WO-A-89/00557. The tridentate tris-thiols of Holm et al. (see JACS 112: 8015–8023 (1990) and JACS 110: 2484–2494 (1988)) also may be used.

For adminstration to human or animal subjects, the chelated compounds of formulae (I) and (II) will conveniently be formulated together with pharmaceutical or veterinary carriers or excipient. The contrast media of the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or administration directly into a body cavity having an external voidance duct, for example the gastrointestinal tract, the bladder and the uterus. Thus the media of the invention may be in conventional pharmaceutical adminstration forms such as tablets, coated tablets, capsules, powders, solutions, suspensions, dispersions, syrups, suppositories etc; solutions, suspensions and dispersions in physiologically acceptable carrier media, e.g. water for injections, will however generally be preferred. Where the medium is formulated for parenteral administration, the carrier medium incorporating the multinuclear complex is preferably isotonic or somewhat hypertonic. Moreover, media for parenteral administration will preferably contain small quantities, e.g. 0.01 to 10 mole percent relative to the multinuclear complex of free chelants or of weak chelate complexes with physiologically tolerable chelated species (e.g. $Ca^{2+}$); small additions of sodium or calcium salts may also advantageously be made.

For use as X-ray contrast media, the media of the invention should generally have a heavy atom content of 1 millimole/l to 5 mole/l, preferably 0.1 to 2 mole/l. Dosages of from 0.5 to 1.5 mmoles/kg will generally be sufficient to provide adequate contrast although dosages of 0.8 to 1.2 mmoles/kg will normally be preferred.

For scintigraphy, dosages of the radioactive species will generally be lower.

Thus in summary the present invention provides a particularly effective means by which contrast media efficiency may be enhanced by increasing the relative proportion of molecular volume that is occupied by the contrast enhancing heavy metal atoms.

The present invention will now be illustrated further by the following non-limiting Examples (all ratios and percentages are by weight and all temperatures are in degrees Celsius unless specified otherwise). The compounds $W(CO)_6$ (Strem), iodine (Strem), $(R_4N)I$ (R=Pr, Bu; Aldrich), $(Ph_4P)I$ (Aldrich) and $Ag(CF_3SO_3)$ (Aldrich) were used without further purification. Both $W(CO)_6$ and iodine were ground with a mortar and pestle prior to use. Solvents were distilled from the appropriate drying agent and degassed prior to use. Solid state reactions were performed in pyrex tubes with dimensions i.d.×o.d.×1=13×19×260 mm. Except for the preparations of $(Pr_4N)$ $[W_5I_{13}]$·THF, $(Bu_4N)$ $[W_5(C)I_{13}]$, and $(Bu_4N)_2[W_6I_{14}]$, reactions in solution were carried out under a pure dinitrogen atmosphere using standard Schlenk techniques.

EXAMPLE 1

Synthesis of "Phase A"

An intimate mixture of 2.0 g (5.7 mmol) of $W(CO)_6$ and 10 g (39 mmol) of $I_2$ was added to a pyrex tube, degassed, and connected to an oil bubbler. The reaction mixture was heated in an oil bath at 140° C. until the evolution of CO ceased (ca. 3 h). The resulting black-gray solid (Phase A) was removed from the tube and pulverized. The solid was washed repeatedly with ether until the filtrate became colorless (ca. 300 ml), at which point 1.8 g of black solid (washed Phase A) remained.

EXAMPLE 2

Synthesis of $(Bu_4N)$ $[W_3I_9]$

Washed Phase A (1.8 g) was added to 200 mL of THF and stirred overnight. The solution was filtered through Celite, and solid $(Bu_4N)I$ (0.50 g, 1.4 mmol) was added to the deep red filtrate. The solution was stirred for an additional 8 h, and concentrated to ca. 5 mL under reduced pressure. The solution was layered with 25 mL of ether and maintained at −15° C. overnight. The resulting red-brown solid was filtered and washed quickly with 10 mL of ethanol. The solid was then washed with ether (3×10 mL), dried under vacuum, and recrystallized by slow evaporation of a dichloromethane solution to yield 0.38 g (11% based on $W(CO)_6$) of red-black crystalline product. Absorption spectrum (THF): $\lambda_{max}$ ($\epsilon_m$): 278 (30,400) , 308 (15,000), 337 (sh, 12,300), 428 (sh, 8130), 455 (sh, 8860), 510(4730), 604 (sh, 1060), 721 (468) nm. Anal. Calcd. for $C_{16}H_{36}I_9NW_3$: C, 9.93; H, 1.87; I, 58.99; N, 0.72; W, 28.49. Found: C, 10.03; H, 1.93; I, 58.92; N, 0.75; W, 28.32.

EXAMPLE 3

Synthesis of $W_4I_{13}$

The pyrex tube containing Phase A was sealed under vacuum, heated in a tube furnace at 165° C. for 50 h, and cooled to room temperature at a rate of 0.2° C./min. The tube was opened (see Caution 1), the contents were removed and washed with aliquots of ether to remove unreacted iodine. The black solid was then washed with THF (5×50 mL) and more ether (3×5 mL), leaving 0.30 g (8.8% based on $W(CO)_6$) of black microcrystalline product. Anal. Calcd. for $I_{13}W_4$: I, 69.17; W, 30.83. Found: I, 69.51; W, 30.41. Caution 1. Although the majority of the CO is expelled in the synthesis of Phase A, the reaction tube is highly pressurized with CO when removed from the furnace. To minimize blowout, the tube is carefully scored with a metal file and wrapped inside thick foam rubber tubing. The tube is then opened in a well-ventilated hood behind a shield by striking it carefully once with a hammer.

EXAMPLE 4

Synthesis of "Phase B"

The pyrex tube containing Phase A was sealed under vacuum and heated in a tube furnace at 200° C. for 50 h; it was then cooled (0.2° C./min) to room temperature. The tube was opened (see Caution 1) and its contents were removed and pulverized. The black-gray solid (unwashed Phase B) was washed with 200 mL aliquots of ether to remove unreacted iodine. When the filtrates became colorless, 2.1 g of a dark blue-black solid (Phase B) remained.

EXAMPLE 5

Synthesis of $(Pr_4N)[W_5I_{13}]THF$

Phase B (1.75 g) was added to 200 mL of ethanol over the course of 30 min. The dark green suspension was stirred for 18 h at room temperature, during which time all the solid dissolved. Excess $(Pr_4N)I$ (0.50 g, 1.6 mmol) was added as a solid to the solution, causing an immediate precipitation of a blue solid. The solution was stirred for 30 min; the solid was collected by filtration and washed with ethanol (15 mL) and ether (2×10 mL). The solid was dried under aspirator vacuum and was recrystallized from THF/hexane at −15° C. to afford 0.98 g (31% based on $W(CO)_6$) of blue microcrystalline solid. Absorption spectrum (THF): $\lambda_{max}$ ($\epsilon_m$): 298 (33,700), 347 (sh, 13,900), 370 (sh 11,800), 423 (sh, 7720), 478 (5880), 524 (4990), 588 (4190), 623 (4080), 722 (2900), 844 (2050) nm. Anal. Calcd. for $C_{16}H_{36}I_{13}NOW_5$: C, 6.79; H, 1.28; I, 58.34; N, 0.50; W, 32.53. Found: C, 6.48; H, 1.24; I, 58.84; N, 0.52; W, 32.79.

EXAMPLE 6

Synthesis of $(Pr_4N)_2[W_5I_{13}]$

A 100 mL Schlenk flask was charged with 1.0 g (0.35 mmol) of $(Pr_4N)[W_5I_{13}]THF$, 0.056 g (0.86 mmol) of Zn dust, and 0.22 g (0.70 mmol) of $(Pr_4N)I$. The contents of the flask were thoroughly degassed, and 30 mL of dichloromethane was added. The reaction mixture was stirred for 24 h, during which time a color change from deep green to brown-red was observed. The mixture was filtered through Celite and was concentrated to ca. 3 mL under vacuum. The solution was layered with 10 mL of ether and maintained at −15° C. overnight. The reddish brown solid was collected by filtration, washed with ethanol (10 mL) and ether (2×10 mL), and dried in vacuum. This material was recrystallized from dichloromethane/ether to afford the product as 0.76 g (74%) of a microcrystalline black solid. Absorption spectrum (THF): $\lambda_{max}$ ($\epsilon_m$): 348 (12,500), 408 (sh, 7630), 535 (3760) nm. EPR ($CH_2Cl_2$, 120K) : axial, g=1.97, peak-to-peak width 260 G. Anal. Calcd. for $C_{24}H_{56}I_{13}N_2W_5$: C, 9.79; H, 1.92; I, 56.08; N, 0.95; W, 31.26. Found: C, 9.62; H, 1.85; I, 56.21; N, 0.92; W, 31.36.

EXAMPLE 7

Synthesis of $(Pr_4N)_2[W_5I_8(CF_3SO_3)_5]$

A mixture of 0.41 g (0.14 mmol) of $(Pr_4N)_2[W_5I_{13}]$ and 0.21 g (0.78 mmol) of $Ag(CF_3SO_3)$ was stirred in 35 mL of dichloromethane for 18 h in the absence of light. A gradual color change from brown-red to purple occurred and AgI precipitated. The reaction mixture was filtered through Celite, and the filtrate was concentrated to 5 mL under reduced pressure. Ether (25 mL) was carefully layered on top of the solution, resulting in the formation of black crystals over the course of 24 h. The crystalline product was collected and washed with 2×10 mL of ether to afford 0.22 g (51%) of pure product. Absorption spectrum (THF): $\lambda_{max}$ ($\epsilon_m$) 291 (sh, 11,600), 358 (sh, 6770), 439 (3960), 598 (1850) nm. The compound was identified by a single crystal X-ray structure determination.

EXAMPLE 8

Synthesis of $(Bu_4N)[W_5(C)I_{13}]THF$

Cesium iodide (1.25 g, 4.81 mmol) was added to the pyrex tube containing Phase A. The tube was then sealed under vacuum and heated in a steel-lined tube furnace at 300° C. (see Caution 2) for 50 h; it was then cooled (0.2° C./min) to room temperature. The tube was opened (see Caution 1) and washed with 200 mL of ether to remove unreacted iodine. When the filtrates became colorless, 1.2 g of a brown-black partially crystalline solid remained. The FAB-MS of a dichloromethane-soluble portion of this solid revealed the presence of $Cs[W_5(C)I_{13}]$, $Cs_2[W_6I_{14}]$, and cesium iodides that could not be fully identified. The black solid was stirred overnight in 150 mL of acetonitrile to give a deep orange solution. The solution was filtered, and 0.75 g (2.0 mmol) of solid $(Bu_4N)I$ was added to the filtrate. The red precipitate which immediately separated was collected by filtration and washed with ether (2×10 mL). The filtrate was evaporated to dryness to give a red-orange solid residue. The combined solids were partially dissolved in 50 mL of THF and the solution was filtered. The undissolved red solid was washed with ethanol (5×10 mL) and was recrystallized from THF/hexane to give the product as 0.18 g (5.5% based on $W(CO)_6$) of a red microcrystalline solid. Absorption spectrum (THF): $\lambda_{max}$ ($\epsilon_m$) 329 (sh, 33,900), 403 (sh, 11,200), 442 (9830) nm. Anal. Calcd. for $C_{21}H_{44}I_{13}NOW_5$: C, 8.71; H, 1.53:I, 56.97; N, 0.48; W, 31.75. Found: C, 8.54; H, 1.46; I, 57.06; N, 0.49; W, 31.68. Caution 2. There is some risk of explosion when heating Phase A in a sealed pyrex tube at 300° C. Consequently, it is advised that the tube furnace be located in a well-ventilated explosion-proof hood. A steel-lined process tube is also recommended to minimize furnace damage in the event of an explosion. Heating at temperatures above 300° C., changing the dimensions of the pyrex tube, or scaling up the reaction may all result in explosions, and are cautioned against.

EXAMPLE 9

Synthesis of $W_6I_{12}$

Phase B (0.62 g) was sealed in a pyrex tube under vacuum and heated in a tube furnace at 550° C. for 50 h. The tube was cooled to room temperature at a rate of 0.2° C./min and opened. The product as 0.23 g (25% based on $W(CO)_6$) of an orange solid is deposited at one end of the tube and some free iodine is found at the other end. The compound was identified by a single crystal X-ray structure determination, and subsequent X-ray powder diffraction patterns.

EXAMPLE 10

Synthesis of $W_6I_{16}$

Unwashed Phase B (8.0 g) was sealed in a pyrex tube under vacuum. The tube was heated in a tube furnace at 550° C. for 50 h, and was cooled to room temperature at a rate of 0.2° C./min. The tube was opened and the reaction product was washed with 100 mL of ether. The product was obtained as 1.3 g (44% based on $W(CO)_6$) of red-brown solid. The compound was identified by a single crystal X-ray structure determination, and subsequent X-ray powder diffraction patterns.

EXAMPLE 11

Synthesis of $(Bu_4N)_2[W_6I_{14}]$

Phase B (1.6 g) and KI (1.0 g, 6.0 mmol) were sealed under vacuum in a pyrex tube and heated at 550° C. for 65 h. The tube was cooled to room temperature (0.2° C./min) and opened. The black-orange product was completely dissolved in 125 mL of ethanol to give a deep orange solution, which was filtered. Addition of 0.50 g (1.4 mmol) of $(Bu_4N)I$ to the filtrate caused the immediate precipitation of a yellow-orange solid. This material was collected by filtration and washed with cold ethanol (2×10 mL) and ether (10 mL). The product was obtained as 0.95 g of a yellow-orange solid; the yield is 30% based on $W(CO)_6$ used in the preparation of Phase A. FAB-MS: m/z 3122 $([(Bu_4N)(W_6I_{14})]^{1-})$, m/z 2881 $([HW_6I_{14}]^{1-})$. Unit cell parameters obtained from a single crystal match those reported previously for this compound.

EXAMPLE 12

Synthesis of $(Bu_4N)_2[W_6I_8(CF_3SO_3)_6]$

A mixture of 250 mg (74 mmol) of $(Bu_4N)_2[W_6I_{14}]$ and 135 mg (525 mmol) of $Ag(CF_3SO_3)$ in 30 mL of dichloromethane was stirred for 18 h in the absence of light, and filtered through Celite to remove AgI. The bright yellow filtrate was concentrated to ca. 3 mL under reduced pressure; 20 mL of ether was carefully layered on top of the solution. Bright yellow crystals separated within hours; these were filtered and washed with ether (3×10 mL) to afford 0.21 g (81%) of pure product. Absorption spectrum $(CH_2Cl_2)$: $\lambda_{max}$ $(\epsilon_m)$ 289 (12,000), 343 (sh, 4830) nm. Anal. Calcd. for $C_{38}H_{72}F_{18}I_8N_2O_{18}S_6W_6$: C, 13.04; H, 2.07; F, 9.78; I, 29.03; N, 0.84; S, 5.49; W, 31.56. Found: C, 13.08; H, 2.05; F, 9.65; I, 28.91; N, 0.86; S, 5.38; W, 31.42.

We claim:

1. A process for the preparation of a compound of formula $$M_n B_u A_v \qquad (I)$$

where $M_n B_u A_v$ is a multinuclear entity; each M is a heavy metal atom selected from W, Mo, Ta, Nb and Hf, each metal atom M is covalently bonded to at least one other atom; each B is a bridging atom covalently bonded to at least two metal atoms M; each A which may the same or different is a non-bridging atom covalently bonded to a metal atom M; n and u are positive integers not less than 2; and v is zero or a positive integer, or a salt thereof, comprising reacting $M(CO)_6$ and $I_2$ for a time and at a temperature sufficient to form a metal/iodine cluster, and optionally displacing one or more bridging or non-bridging iodine atoms in said cluster with one or more further atoms or radicals to form a modified cluster and/or formation of a salt of said cluster or modified cluster.

2. A process as claimed in claim 1 wherein n in the compound of formula (I) is from 2 to 6.

3. A process as claimed in claim 1 wherein M is W.

4. A process as claimed in claim 1 wherein A is iodine.

5. A process as claimed in claim 1 wherein the temperature is from 140° C. to 220° C.

6. A process as claimed in claim 1 wherein the temperature is from 220° C. to 550° C.

* * * * *